(12) United States Patent
Almirall et al.

(10) Patent No.: US 10,329,597 B2
(45) Date of Patent: Jun. 25, 2019

(54) **METHOD FOR DETECTION OF *PSEUDOMONAS AERUGINOSA* (PA) USING VOLATILE BIOMARKERS**

(71) Applicants: Jose Almirall, Miami, FL (US); Wen Fan, Athens, OH (US); Kalai Mathee, Miami Beach, FL (US)

(72) Inventors: Jose Almirall, Miami, FL (US); Wen Fan, Athens, OH (US); Kalai Mathee, Miami Beach, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 315 days.

(21) Appl. No.: 14/935,882

(22) Filed: Nov. 9, 2015

(65) Prior Publication Data

US 2016/0138069 A1    May 19, 2016

Related U.S. Application Data

(60) Provisional application No. 62/081,217, filed on Nov. 18, 2014.

(51) Int. Cl.
*C12Q 1/04*    (2006.01)

(52) U.S. Cl.
CPC ........... *C12Q 1/04* (2013.01); *G01N 2333/21* (2013.01)

(58) Field of Classification Search
None
See application file for complete search history.

(56) References Cited

U.S. PATENT DOCUMENTS

2014/0260974 A1    9/2014    Almirall et al.

OTHER PUBLICATIONS

Scott-Thomas et al., BMC Pulmonary Medicine 10: 56 (2010).*
Fan et al., Anal. Bioanal. Chem. 406: 2189-2195 (2014; published online Oct. 20, 2013).*
Koziel et al., J. Air and Waste Management Assoc. 55(8): 1147-1157 (2005).*
Filipiak et al., BMC Microbiol. 12: 113 (2012).*
Farag et al., Phytochemistry 67: 2262-2268 (2006).*
Filipiak, W. et al., "Release of volatile organic compounds (VOCs) from the lung cancer cell line CALU-I in vitro," *Cancer Cell International*, 2008, 8:17.

* cited by examiner

*Primary Examiner* — Erin M. Bowers
(74) *Attorney, Agent, or Firm* — Saliwanchik, Lloyd & Eisenschenk

(57) ABSTRACT

A method of determining the presence of *Pseudomonas* involves establishing a gaseous headspace over a surface suspected of containing at least one *Pseudomonas* strain and contacting at least a portion of the gaseous headspace with a capillary microextraction of volatiles (CMV) sampling device to absorb at least one component of the headspace by the CMV sampling device. The component loaded CMV sampling device is coupled to an injection port of an analytical device where the components are desorbed into the analytical device, where components are separated, detected, and identified to determine if one or more of the identified components is a biomarker for at least one *Pseudomonas* strain.

5 Claims, 4 Drawing Sheets

METHOD FOR DETECTION OF PSEUDOMONAS AERUGINOSA (PA) USING VOLATILE BIOMARKERS

CROSS-REFERENCE TO A RELATED APPLICATION

This application claims the benefit of U.S. Provisional Application Ser. No. 62/081,217, filed Nov. 18, 2014, the disclosure of which is hereby incorporated by reference in its entirety, including all figures, tables and drawings.

BACKGROUND OF INVENTION

Breath analysis is a potential revolution in lung and other disease diagnostics since the collection of exhaled breath is a safe, non-invasive, easy and simple procedure and each individual can provide breath that contains information regarding their own internal state.

Cystic Fibrosis (CF) is the most common genetic disorder in the white population, affecting 1 in 3300 live Caucasian births. This genetic disorder disables a transmembrane chloride conductance regulator (CFTR) that regulates the balance of salts in epithelia cells that exist in many of the glands and affects multiple systems, including lung, pancreas, and gastrointestinal systems. In lung disease, deficiency in CFTR causes obstruction of submucosal glands and distal airways with thick tenacious secretions against bacterial infection. Bacteria that most often colonize and infect the lungs of people with CF are *Haemophilus influenza, Staphylococcus,* and *Pseudomonas aeruginosa* (*P. aeruginosa*) and among these three, *Pseudomonas* family has a reputation of being particularly dangerous, which correlates with declining lung function and high mortality rates.

*Pseudomonas aeruginosa* is a Gram negative bacterium that produces an odor (grape-like) which has been identified as 2-aminoacetophenone (2-AA). This compound was once detected in the headspace of *Escherichia coli* (*E. coli*) cultures, but not in other respiratory pathogens and, therefore, was used as a volatile biomarker for infection and/or colonization in the lung. However, 2-AA was also found in the breath samples of uninfected individuals shortly after eating certain foods, such as corn, dairy, honey products and wine. Other than 2-AA, 2-nonanone, 2,4-dimethyl-1-heptene, 1-heptene, isopentanol and limonene have been found in the headspace of spontaneously expectorated sputum with *P. aeruginosa*.

Headspace samplers are used to introduce a portion of the headspace gas present over any type of sample, either gas, liquid or solid, confined in a closed system, such as a sealed vial. The vial can be maintained at room or any other temperature to establish an equilibrium composition of volatiles above the sample. Advantageously, headspace sampling allows the selective sampling of volatile species while leaving the complex matrix in the vial without contamination during sampling. Although headspace sampling is useful for analysis of samples from a complicated matrix, the low concentration of components in a headspace and the small sample volume can be problematic for detection of trace compounds.

Hence, although the headspace sampling over *P. aeruginosa* can be carried out by headspace analysis, a consistent and sensitive protocol for the detection of *P. aeruginosa* where the identification of the specific strain remains a goal that can aid in the treatment of the disorder.

BRIEF SUMMARY

A method of determining the presence of *Pseudomonas* involves establishing a gaseous headspace over a surface suspected of containing at least one *Pseudomonas* strain and contacting at least a portion of the gaseous headspace with a capillary microextraction of volatiles (CMV) sampling device to absorb at least one component of the headspace by the CMV sampling device. The component loaded CMV sampling device is coupled to an injection port of an analytical device where the components are desorbed into the analytical device where components are separated, detected, and identified to determine if one or more of the identified components is a biomarker for at least one *Pseudomonas* strain. The CMV sampling device is a glass capillary tube containing a fibrous glass material that has been coated with a sol-gel derived PDMS coating. The gaseous headspace can be forced though the CMV sampling device by establishing a pressure drop from an inlet of the CMV sampling device to an outlet of the CMV sampling device by imposing a positive pressure at the inlet or a negative pressure at the outlet of the CMV sampling device. The analytical device can be a gas chromatograph coupled to a mass spectrometer (GC/MS). The detection of possible *Pseudomonas* can be by the detection of the biomarker 2-aminoacetophenone (2-AA) and/or the biomarker undecene. The *Pseudomonas* can be at the internal surface of lungs of a patient. In this case, the gas contained in the lungs can be exhaled through the CMV sampling device for absorption of its components. A holder can be used to position one or more CMV sampling devices in communication with at least a portion of the exhale.

DETAILED DISCLOSURE

Figure 1:
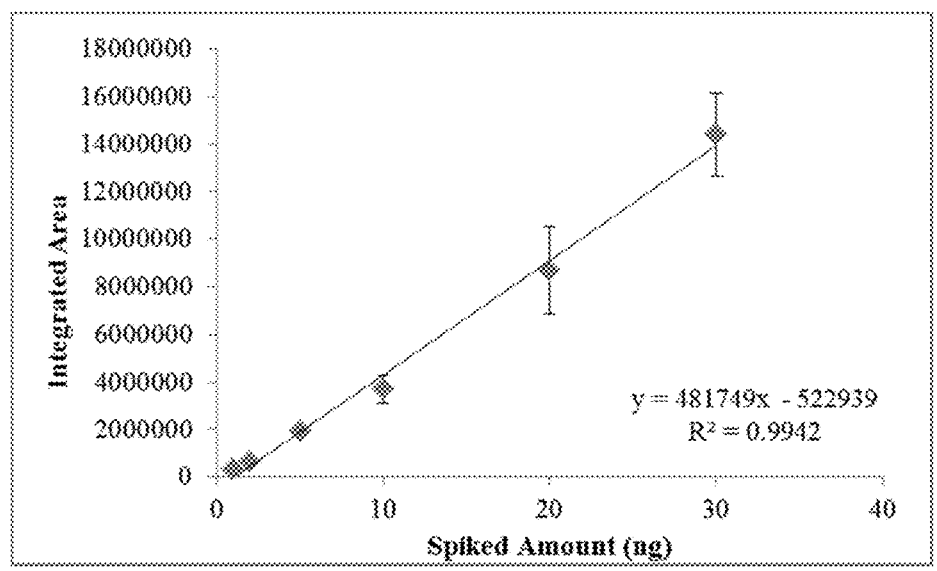
FIG. 1 shows a calibration curve for 2-aminoacetophenone (2-AA) by GC/MS.

Embodiments of the invention are directed to a method of detecting biomarkers of *Pseudomonas aeruginosa* in a patient or other environment. For example, the contents of the lungs can be sampled by collecting volatile components in a lung exhale sample, either from a relatively large volume collected from one or more exhales or sampled directly during the exhaling of the patient. In embodiments of the invention, the biomarkers are concentrated using a capillary microextraction of volatiles (CMV) technique where volatiles and semi-volatiles in a headspace are concentrated and the concentrated sample analyzed by coupling with a high throughput nearly quantitative analytical technique for unambiguous identification of compounds in the headspace, such as gas chromatography coupled to mass spectrometry (GC/MS).

The CMV sampling devices are as those described in U.S. patent application Ser. No. 14/206,250 entitled "Capillary Microextraction of Volatiles (CMV)" and incorporated herein in its entirety. The CMV sampling devices use sol-gel polydimethylsiloxane (PDMS) coated microglass fibers as the sampling/pre-concentration sorbent. These sorbents comprise fibers that are stacked in open-ended capillary tubes. In this manner the device allows dynamic headspace sampling by forcing the gaseous headspace through the device when connected to means of drawing or discharging the headspace gases through the CMV sampling device, for example, using a hand-held vacuum pump. In an embodiment of the invention, the CMV sampling device can be fitted into a thermal desorption probe for thermal desorption of the extracted volatile compounds into a gas chromatography-mass spectrometer (GC-MS) unit.

In embodiments of the invention, at least one CMV sampling device is in communication with the headspace of a body suspected of containing *Pseudomonas aeruginosa* or other *Pseudomonas* strain. The CMV sampling device can be extended over the headspace in any fashion where the headspace is the air or other gaseous environment over a surface having a *Pseudomonas* population. The headspace can be within a container or be open to the atmosphere. The air of the head space can be forced through the CMV sampling device by providing a positive pressure to the vicinity of the headspace with a flow of gas, including the gas over the headspace, which is delivered to an airspace proximal end of the CMV sampling device. Alternatively, a negative pressure can be provided to an end of the tube distal to the headspace and gas that includes the headspace gas is drawn into the CMV sampling device. The negative pressure can be provided by a vacuum pump, the drawing of a syringe, a venturi connected with a second source of fluid, or any other means of generating a pressure drop from an inlet end of the CMV sampling device to the outlet end of the CMV sampling device. The sampling of the headspace can be for a period of time where a sufficient quantity of the biomarker is absorbed on the microextraction media of the CMV sampling device. For example, the gas including the headspace gas can be contacted with the CMV sampling device for 30 seconds, 1 minute, 2 minutes, 3 minutes, 4 minutes, 5 minutes, 6 minutes, 7 minute, 8 minutes, 9 minutes, 10 minutes, 15 minutes, or more.

In an embodiment of the invention, one or more CMV sampling devices can be included in a holder by which a patient can exhale through the CMV sampling device. The holder can assist the flow of air through the CMV sampling device as needed or divert only a portion of the exhaled air through the CMV sampling device. The holder can be designed to draw the exhaled air into an expandable bladder or body that allows the bladder or body collected exhaled air to be forced through the CMV sampling device after an exhale at a rate of gas flow that is significantly longer than would be possible for direct exhalation by the patient. Coupling with a second bladder or body can permit the passing of the headspace sample back and forth through the CMV sampling device a plurality of times until the components are effectively quantitatively absorbed in the CMV sampling device. The holder can couple the nose and/or the mouth of the patient such that at least a portion of the exhaled contents of the lung is forced through the CMV sampling device.

In embodiments of the invention, the biomarker loaded CMV sampling device can be placed in an injection port of an analytical device that permits the introduction of the absorbed species on the microextraction medium within the CMV sampling device onto an instrument that performs the separation of the extracted components, including the one or more biomarkers, their detection and their identification. The instrument can be, for example, but not limited to, a gas chromatograph coupled to a mass spectrometer (GC/MS). In this manner, no reference standards are required for complete analysis of the headspace gas for the testing of the presence of *Pseudomonas*, including *P. aeruginosa*, in the head space.

The analysis can be carried out in a manner where the identity of one or more biomarkers is sufficient to determine the possible presence of the bacteria, or can be carried out where a relative quantification of biomarkers and other components can indicate the *Pseudomonas* and determine or suggest what strain, such as *Pseudomonas aeruginosa*, is present. The analysis can be carried out with a single sample or with a plurality of samples to assure that a false negative or positive indication of the bacteria has occurred. A plurality of samples can be obtained simultaneously or successively.

METHODS AND MATERIALS

An Agilent Technologies 7890A GC system was coupled to a 5975C inert XL mass spectrometry detector (MSD) and a micro-electron capture detector (μ-ECD) by using a two-way splitter with makeup gas connections controlled by a pneumatics control module (PCM). The flow ratio of the MSD to the μ-ECD was controlled at 5 to 1 by using restrictors. Since MSD requires vacuum and μ-ECD is operated under atmospheric pressure, the restrictor limited the flow into the MSD by increase the restrictor's length or diameter. The restrictor used for μ-ECD was a 0.405 m restrictor with an inner diameter of 0.10 mm and the restrictor used for MSD was 1.113 m with an inner diameter of 0.15 mm. The GC front injector was a regular split/splitless port used for direct liquid injection using an autosampler and SPME analysis and the back injector was replaced with a thermal separation probe adapter which was used to thermally desorb the CMV devices at 180° C. The thermal separation probe (Agilent Technologies Inc., Santa Clara, Calif.) was coupled with the GC injector using an adapter.

TABLE 1

GC-MS conditions for headspace analysis using CMV

| | |
|---|---|
| Column type | Agilent Technologies 8 m × 0.25 mm ID × 0.25 μm DB - 5MS UI |
| Carrier gas | Helium at a flow rate of 1.0 mL min$^{-1}$ |
| Split ratio | 5:1 |
| Injector Temperature | 180° C. |
| Column oven parameters | 40° C., hold for 1 min. |
| | 200° C. at 15° C. min$^{-1}$, hold for 1 min |
| | 240° C. at 15° C. min$^{-1}$, hold for 6.5 min |
| | 270° C. at 25° C. min$^{-1}$, hold for 0 min |
| | 280° C. at 5° C. min$^{-1}$, hold for 4 min |
| MS Transfer Line temperature | 280° C. |
| MS Ion Trap Temperature | 180° C. |
| Running Time | 29.33 min |
| Run Cycle | 35 min |

Sorbent-coated glass filters were prepared as follows: glass fiber filter circles with diameters of 4.25 cm, 3.3 cm and 2.4 cm (G6, Fisherbrand, Pittsburgh, Pa.) were prepared with a similar activation procedure in the literature. The glass fiber filters were placed into a 2:1 mixture of concentrated sulfuric acid (Fisher Scientific, Fair Lawn, N.J.) and 30% hydrogen peroxide (Fisher Scientific, Fair Lawn, N.J.) at room temperature for 10 min. The solution was decanted and the substrates rinsed with deionized water until neutral.

The filters were submerged into 1 M NaOH solution for 1 h and rinsed with deionized water until neutral by litmus paper. The cleaned filters were placed in an oven at 80° C. for 2 h to dry with the compact side facing down the matte side of the aluminum foil to avoid breakage of the filter. A sol-gel PDMS solution was prepared using: 2.060 g vinyl terminated polydimethylsiloxane (vt-PDMS) in 8 mL of dichloromethane DCM, 1.10 mL of methyltrimethoxysilane (MTMOS) and 0.535 g of polymethylhydrogensiloxane (PMHS). Subsequently 0.875 mL of TFA (Acros) (5% water v/v) was added and the solution was vortexed for 30 min. To evenly coat a filter, the prepared glass fiber filter circle was placed on top of a cut glass slide held by vacuum on the chuck of a spin-coater (Laurell Technologies, North Wales, Pa.). Coating solution of 1.2, 1.0 and 0.8 mL were deposited on the glass fiber filter circles of 4.25 cm, 3.3 cm and 2.4 cm diameter, respectively, and coated with s spin coater programmed at 1000 rpm for 60 s. The deposited sol-gel PDMS was cured to form PSPME coated filters, placed in the vacuum desiccator for 1 h, dipped for 5 min in DCM, and gelated in an oven at 40° C. overnight. The PSPME coated filters were placed in a GC oven in a nitrogen atmosphere at 120° C. for 1 h, 240° C. for 1 h, and 300° C. for 3 h for final curing. After the final curing process, the filters were cooled in the oven using a controlled program of 8° C./min to prevent cracking of the coating.

The PSPME coated filters were cut into about 2 mm by 2 cm rectangular strips. A glass capillary (Wiretrol II, Broomall, Pa.) having an inner diameter of 2 mm and cut into 2 cm lengths and filled with seven of the about 2 mm-wide and 2 cm long strips to form the CMV device. The CMV devices having two open ends were connected to a hand-held vacuum pump that operated at the flow rate 1.5 liters per minute (LPM) to promote airflow through the CMV device while extracting compounds onto the sol-gel PDMS coated glass fiber filters. The CMV devices were then placed into a commercial thermal desorption unit (Agilent Technologies, Santa Clara, Calif.) to desorb all the accumulated compounds into a GC column for separation and identification with mass spectrum. The CMV device of 2 cm length contains about 0.230 g of coated glass filters. The ~0.05 $m^2$ PDMS coated surface is calculated to contain a phase volume of 50 $mm^3$.

The CMV devices were conditioned in an oven at 250° C. for 1 hour, allowed to cool to room temperature and connected to a hand-held air monitoring vacuum pump (Escort Elf Air Sampling Pump, Zefon International Inc., Ocala, Fla.) that provides a flow through the CMV device of 0.1-1.5 liters per min (LPM). After typical sampling times of between 30 s-1 min, the CMV device was disconnected from the tubing and inserted into a probe for thermal desorption in an Agilent Technologies 7890A GC injector. The thermal separation probe (Agilent Technologies Inc., Santa Clara, Calif.) can be coupled with the GC injector using a commercially available adapter.

All the headspace analysis was accomplished using bacteria cultural plates that included *Pseudomonas aeruginosa*, *Bacillus* strain, *Chromobacterium violaceum*, *Escherichia coli*, and *Serratia marcescen*. The bacteria strains used in this study are listed in Table 2, below. For *P. aeruginosa*, in addition to laboratory modified strains, two clinical isolated strains were obtained. Other bacteria strains were used as negative controls for profiling the signature volatile compounds for *P. aeruginosa* strains.

TABLE 2

Bacteria strains used in headspace analysis of *Pseudomonas aeruginosa*

| Blind ID | Strain ID | Strain | Relevant characteristics |
|---|---|---|---|
| *Pseudomonas aeruginosa* | | | |
| GDT1 | | PAO1 | Prototypic wild type |
| GDT165 | PKM315 | PAOΔampR | In-frame deletion of ampR (PA4109) |
| GDT61 | PKM900 | PAOΔmifS | In-frame deletion of mifS (PA5512) |
| GDT33 | PKM901 | PAOΔmifR | In-frame deletion of mifR (PA5511) |
| GDT34 | PKM902 | PAOΔmifSR | In-frame deletion of mifSR (PA5511-PA5512) |
| GDT170 | PDO300 | PDO300 | PAOmucA22 |
| GDT 163 | GDT 163 | PKM900(pMifS) | PAO1ΔmifS (pMifS); mifS ORF on pPSV37-Gm moved into PAO1ΔmifS; IPTG-inducible; $Gm^R$ |
| GDT 132 | GDT 132 | PKM901 (pMifR) | PAO1ΔmifR (pMifR); mifR ORF on pPSV37-Gm moved into PAO1ΔmifR; IPTG-inducible; $Gm^R$ |
| GDT 152 | GDT 152 | PKM902(pMifSR) | PAO1ΔmifSR (pMifSR); mifSR ORF on pPSV37-Gm moved into PAO1ΔmifSR; IPTG-inducible; $Gm^R$ |
| 466 | | CDN 107 | Clinical isolate from Nigeria |
| 469 | | CDN 118 | Clinical isolate from Nigeria |
| *Bacillus* strains | | | |
| GDT172 | ATCC 35866 | *B. thuringiensis* HD-73 | NRRL B4488 [HD73] |
| GDT175 | ATCC 23857 | *B. subtilis* | ind− tyr+ |
| GDT173 | ATCC 14581 | *B. megaterium* | |
| GDT174 | ATCC 53522 | *B. cereus* UW85 | |
| Other strains | | | |
| GDT69 | CV026 | *Chromobacterium violaceum* | Non-pigment production mutant, production restored with AHLs |
| | | | F− Φ80lacZΔM15 Δ (lacZYA-argF)U169 deoR |

TABLE 2-continued

Bacteria strains used in headspace analysis of *Pseudomonas aeruginosa*

| Blind ID | Strain ID | Strain | Relevant characteristics |
|---|---|---|---|
| GDT5 | DH5α | *Escherichia coli* | recA1 endA1 hsdR17 (rk$^-$ mk$^+$) phoA supE44 λ$^-$ - thi-1 gyrA96 relA1 |
| GDT171 | ATCC 13880 | *Serratia marcescens* | Isolated from pond water |

Growth of bacteria was accomplished in 18-ml culture tubes filled with 5 ml LB medium shaking at 200 rpm at 37° C. for *P. aeruginosa*, 26° C. for *Serratia marcescens*, *Chromobacterium violaceum* and 30° C. for *Bacillus* strains overnight. Further growth was continued on Luria-Bertani (LB) agar plates.

Studies were performed using *P. aeruginosa*, *Chromobacterium violaceum*, and *Escherichia coli*. Dynamic sampling was carried out by suspending the CMV devices over the headspace of LB agar cultural plates and liquid LB medium in test tubes. A first set of blind studies, with different bacteria, was carried out with LB agar cultural plates labeled with their strain ID. The plates were sampled and maintained at room temperature for a day and sampled a second time. In a second set of blind study, 13 different bacteria on LB agar cultural plates labeled with their strain ID were sampled in triplicate on three consecutive days for quantitative analysis. Both blind studies were processed in an identical manner. A series of 2-aminoacetophenone solutions were prepared by diluting 2-aminoacetophenone (Acros Organics, NJ, USA) using Methanol (Fisher Scientific, Fair Lawn, N.J.) with concentrations of 1, 2, 5, 10, 20, and 30 ng μL$^{-1}$. A calibration curve for 2-aminoacetophenone was generated by spiking the calibration solutions on the CMV device and thermally desorbing the 2-AA into the GC-MS, as illustrated in FIG. 1.

Figure 2:
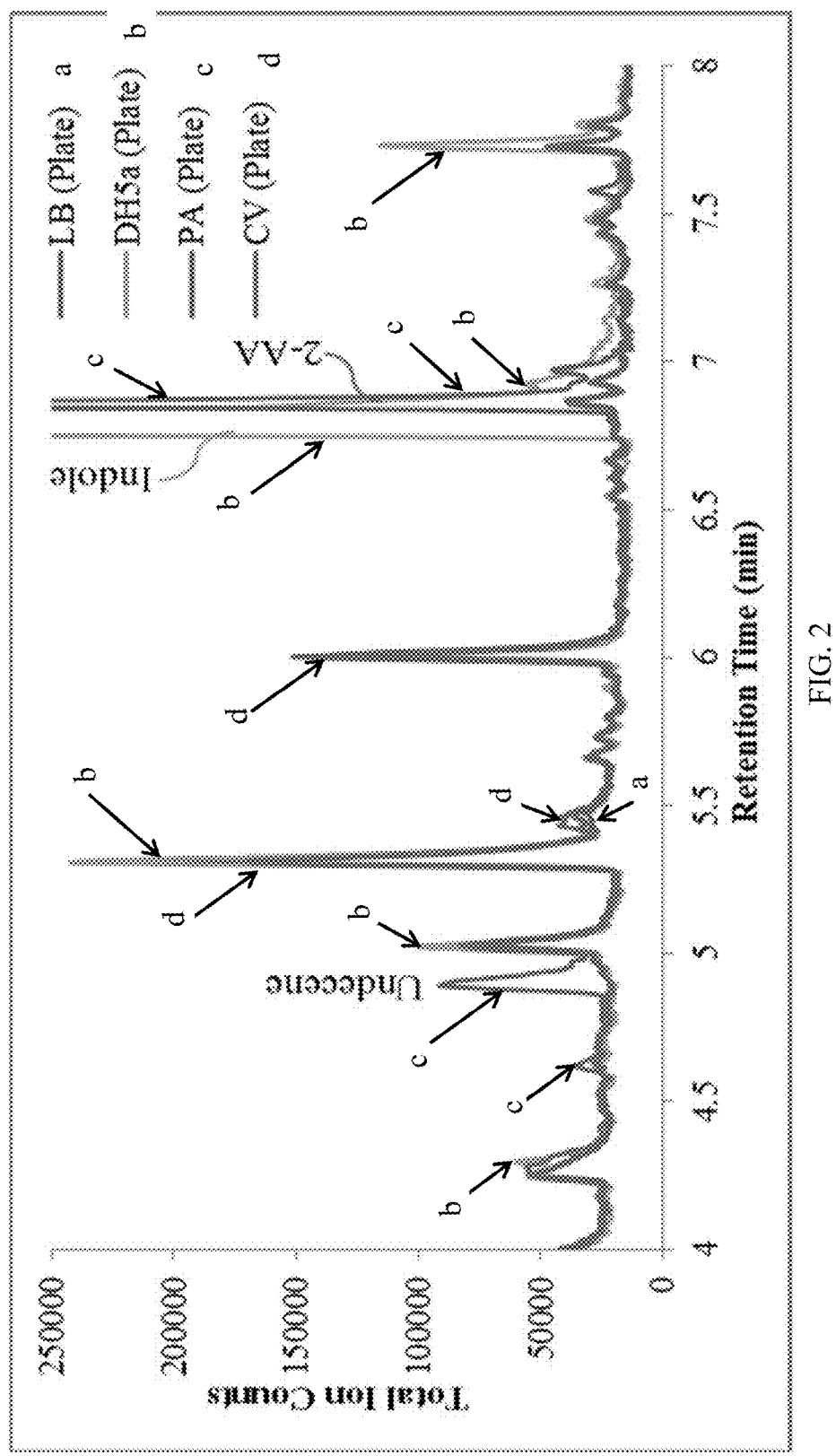
FIG. 2 shows composite GC/MS traces for one minute dynamic samplings of an LB plate, DH5α, PA, and CV cultural plate using a CMV sampling device that displays undecene and 2-AA in the headspace over *Pseudomonas aeruginosa*, according to an embodiment of the invention.
Figure 3:
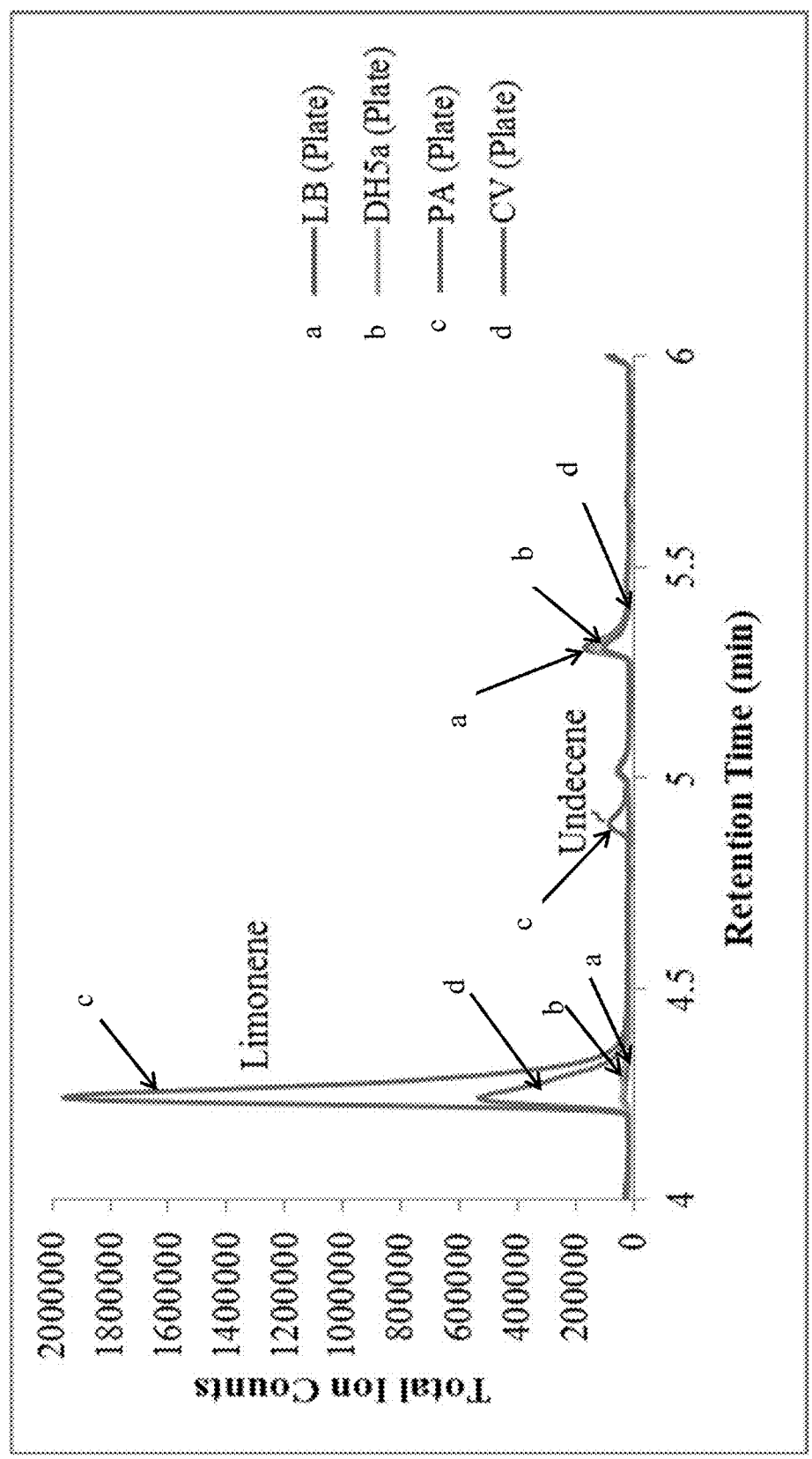
FIG. 3 shows composite GC/MS traces for one minute dynamic samplings with detection of limonene of an LB plate, DH5α, PA and CV plates in the second day sampling of the headspace over *P. aeruginosa* and *C. violaceum*, according to an embodiment of the invention.

The bacteria cultural plates' headspaces were sampled with CMV devices for 1 min. Undecene and 2-aminoacetophenone were detected in *P. aeruginosa*, indole was detected in *E. coli*, as indicated in FIG. 2, and limonene was detected in *P. aeruginosa* and *C. violaceum* plates on second-day sampling, as indicated in FIG. 3.

Figure 4:
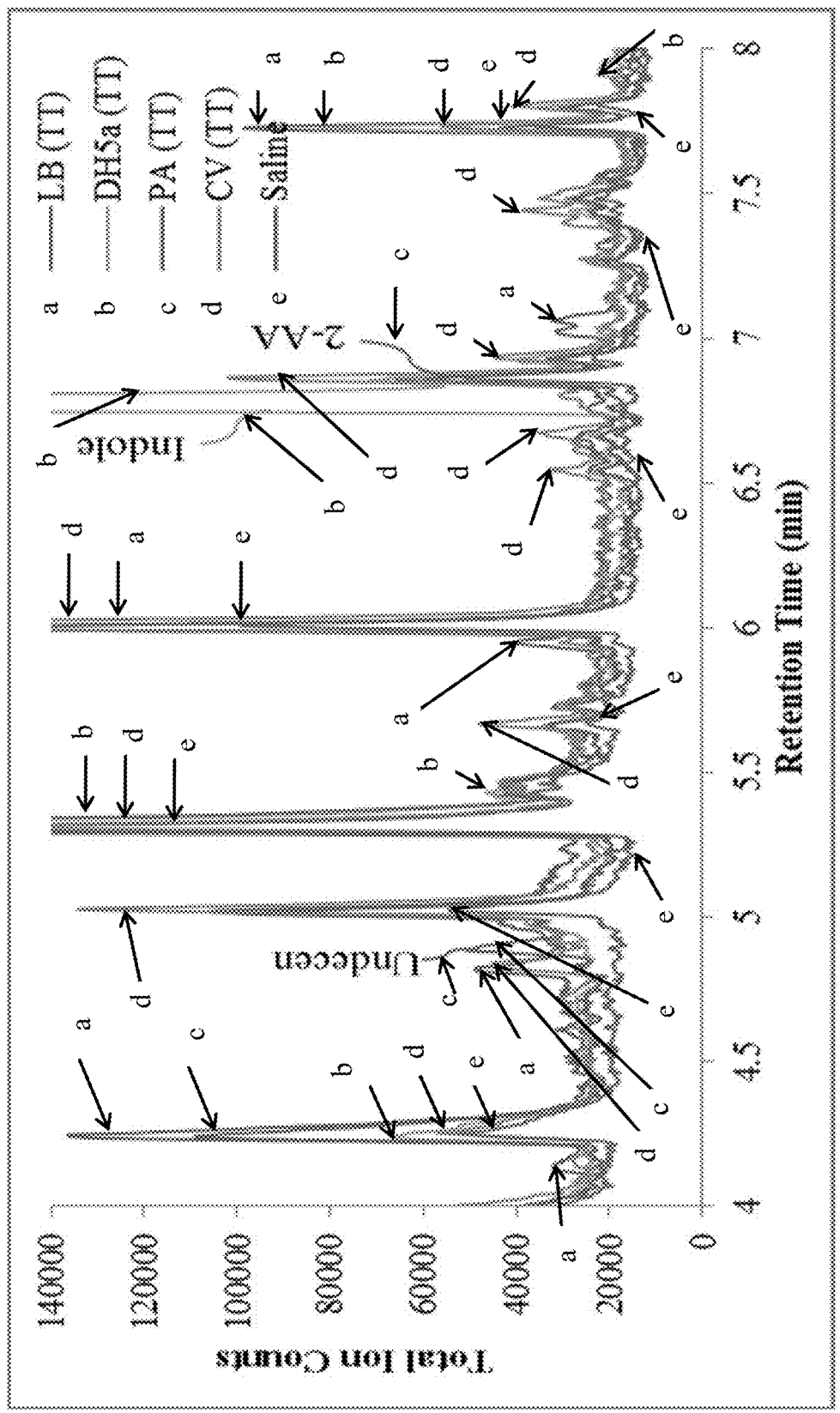
FIG. 4 shows composite GC/MS traces for one minute dynamic headspace sampling of LB, DH5α, PA, CV and Saline in the liquid cultural solutions in a test tube, according to an embodiment of the invention.

Equivalent experiments were performed using 5 ml liquid bacteria cultural medium in a test tube. The 18 mL test tubes provide greater headspace volumes. However, the liquid medium trapped most of the volatile compounds and much smaller signals for undecene and 2-aminoacetophenone were observed, as shown in FIG. 4. All subsequent experiments were carried out using the LB agar cultural plates. Limonene and 2-aminoacetophenone (2-AA) were two compounds consistent with previously published literature as the biomarkers for *P. aeruginosa*.

Initial sampling results using cultural plates indicated by their ID are listed in the second column of Table 2 and the identity was revealed only after the conclusion was made if the bacteria were *Pseudomonas*. The blind studies demonstrated that *P. aeruginosa* is differentiable from other bacteria by using volatile markers. The first set blind study sampled each cultural plate in an initial state and after 24 hours. Table 44 shows volatile compounds detected in 10 different plates immediately after preparation of the plates. The 2-AA signal was indicative of a unique volatile biomarker as limonene was present in all cultural plates. Only plates labeled GDT33, GDT34, and GDT61 were correctly identified as *Pseudomonas*. After 24 hours, the same plates were sampled again and the results are shown in Table 5.

After 24 hours of cultural growth at room temperature, samples GDT1 and PAO also displayed 2-AA into the headspace and were identified as *Pseudomonas*. After the identity of the bacteria was revealed, there were three plates, labeled 466, 469, and PAO300, of *Pseudomonas* strains but did not demonstrate the biomarker. The 466 and 469 samples were clinically isolated strains and PAO300 was genetically modified to possess the characteristics of chronic infection strains common to CF patients. Undecene was detected only in *Pseudomonas* strains and not in other bacteria. Undecene was present only in the headspace of *P. aeruginosa*, 466, 469, and PAO300.

TABLE 4

Volatile compounds detected in the headspace of different cultural plates immediately after preparation of the plates

| Strain | Blind ID | Limonene | Undecene | Acetophenone | 2-AA | Indole |
|---|---|---|---|---|---|---|
| *Pseudomonas* | 466 | + | + | | | |
| *Pseudomonas* | 469 | + | | | | |
| *Pseudomonas* | PAO | + | | | | |
| *Chromobacterium* | GDT69 | + | | | | |
| *Escherichia* | GDT5 | + | | | | + |
| *Pseudomonas* | GDT1 | + | | | | |
| *Pseudomonas* | GDT33 | + | | | + | |
| *Pseudomonas* | GDT34 | + | + | + | + | |
| *Pseudomonas* | GDT61 | + | + | + | + | |
| *Pseudomonas* | PD0300 | + | + | | | |

TABLE 5

Volatile compounds detected in the headspace of different cultural plates 24 hours after preparation

| Strain | Blind ID | Limonene | Undecene | Acetophenone | 2-AA | Indole |
|---|---|---|---|---|---|---|
| *Pseudomonas* | 466 | + | + | | | |
| *Pseudomonas* | 469 | + | + | | | |
| *Pseudomonas* | PAO | + | + | | + | |
| *Chromobacterium* | GDT69 | + | | | | |
| *Escherichia* | GDT5 | + | | | | + |
| *Pseudomonas* | GDT1 | + | | | + | |
| *Pseudomonas* | GDT33 | + | + | | + | |
| *Pseudomonas* | GDT34 | + | + | | + | |
| *Pseudomonas* | GDT61 | + | + | | + | |
| *Pseudomonas* | PD0300 | + | + | + | | |

In addition to differentiating *Pseudomonas*, the second blind study was used to quantify 2-AA in the headspace. The 13 different bacteria were analyzed in triplicate over three consecutive days. The bacterial growth time was not precisely controlled and the colony numbers were not counted. The volatile compounds detected over the 13 samples are indicated in Table 66. Among the 13 strains, 6 were *Pseudomonas*. Using 2-AA as the single marker, 5 out of 6 can be successfully classified. The one not identified was GDT 170, which is PAO300 of the first set blind study. None of the 7 other strains, which included 4 *Bacillus*, 1 *Serratia*, 1 *Escherichia*, and 1 *Chromobacterium* were falsely determined to be a *Pseudomonas* based on the biomarker 2-AA, using CMV-GC-MS. The amount of 2-AA present in different strains was different and the variations within a single strain were large with 3 to 5 ng detected in the headspace. Similar to the first set blind study, undecene was consistently found in the headspace of *Pseudomonas* strains and in no other bacterial strains.

TABLE 6

Volatile compounds detected in the headspace of 13 different bacteria determined in triplicate

| Strain | Blind ID | Undecene (4.62 min) | Indole (6.47 min) | 2-AA (6.55 min) |
|---|---|---|---|---|
| *Pseudomonas* | GDT1 | + | − | 4.6 ± 2.4 ng |
| *Pseudomonas* | GDT165 | + | − | 4.4 ± 1.5 ng |
| *Pseudomonas* | GDT170 | − | − | — |
| *Serratia* | GDT171 | − | − | — |
| *Bacillus* | GDT172 | − | − | — |
| *Bacillus* | GDT173 | − | − | — |
| *Bacillus* | GDT174 | − | − | — |
| *Bacillus* | GDT175 | − | − | — |
| *Pseudomonas* | GDT33 | + | − | 2.9 ± 1.0 ng |
| *Pseudomonas* | GDT34 | + | − | 4.6 ± 1.4 ng |
| *Escherichia* | GDT5 | − | + | — |
| *Pseudomonas* | GDT61 | + | − | 4.3 ± 0.8 ng |
| *Chromobacterium* | GDT69 | − | − | — |

All patent applications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of determining the presence of *Pseudomonas*, comprising:
    establishing a gaseous headspace over a surface suspected of containing at least one *Pseudomonas* strain, the surface comprises the internal surface of lungs of a patient and the gaseous head space comprises the gas contained in the lungs before exhaling;
    providing at least one capillary microextraction of volatiles (CMV) sampling device;
    contacting at least a portion of the gaseous headspace with the CMV sampling device, by exhaling at least a portion of the gaseous head space through the CMV sampling device, and wherein at least one component of the gaseous headspace is absorbed by the CMV sampling device;
    desorbing the at least one component of the headspace from the CMV sampling device into an injection port of an analytical device configured to separate, detect, and identify the at least one component of the head space; and
    determining from the detected and identified at least one component of the headspace the absence or presence of at least one biomarker comprising undecene of at least one *Pseudomonas* strain.

2. The method of claim 1, wherein the CMV sampling device comprises a glass capillary tube containing a fibrous glass material, wherein the fibrous glass material is coated with sol-gel derived polydimethylsiloxane (PDMS) coating.

3. The method of claim 1, wherein the analytical device comprises a gas chromatograph coupled to a mass spectrometer (GC/MS).

4. The method of claim 1, wherein the at least one biomarker comprises 2-aminoacetophenone (2-AA) and undecene.

5. The method of claim 1, further comprising a holder for positioning the at least one CMV sampling device in communication with the gas contained in the lungs upon exhaling.

* * * * *